United States Patent [19]

Fujimori

[11] 4,334,879

[45] Jun. 15, 1982

[54] SAMPLE APPLICATOR

[75] Inventor: Ryo Fujimori, Hachiouji, Japan

[73] Assignee: Olympus Optical Co., Ltd., Tokyo, Japan

[21] Appl. No.: 146,182

[22] Filed: May 2, 1980

[30] Foreign Application Priority Data

May 4, 1979 [JP] Japan .............................. 54/59754[U]

[51] Int. Cl.³ .................... G01N 1/10; G01N 27/26
[52] U.S. Cl. .................. 23/230 R; 23/230 B; 422/99; 422/100; 422/104
[58] Field of Search .............. 422/99, 100, 104, 56, 422/57, 58; 23/230 R, 230 B; 73/421 R

[56] References Cited

U.S. PATENT DOCUMENTS

| | | | |
|---|---|---|---|
| 3,443,903 | 5/1969 | Haack et al. | 422/56 X |
| 3,798,004 | 3/1974 | Zerachia | 422/56 |
| 3,881,873 | 5/1975 | Klowden | 422/56 |
| 3,980,437 | 9/1976 | Kishimoto et al. | 422/56 X |
| 4,076,502 | 2/1978 | Dugle et al. | 422/58 X |
| 4,126,417 | 11/1978 | Edwards | 422/56 |

Primary Examiner—Ronald Serwin
Attorney, Agent, or Firm—Cushman, Darby & Cushman

[57] ABSTRACT

A sample applicator comprising a holder and an applicator blade of porous material formed as a rectangular plate and mounted to an end of holder, the sample applicator being arranged to apply a sample onto a film by making the applicator blade absorb the sample and, then, pushing the applicator blade onto the film.

1 Claim, 10 Drawing Figures

| PRIOR ART | PRIOR ART | PRIOR ART | PRIOR ART |
|---|---|---|---|
| FIG. 1A | FIG. 1B | FIG. 2A | FIG. 2B |
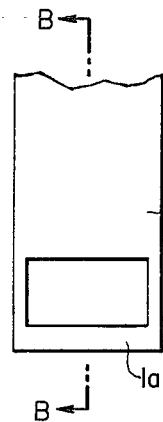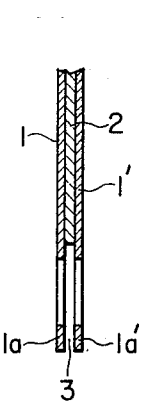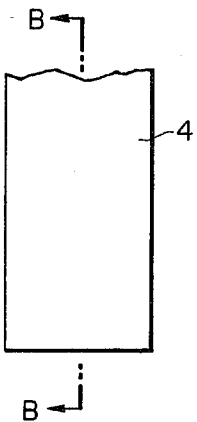
FIG. 3A    FIG. 3B    FIG. 4    FIG. 5
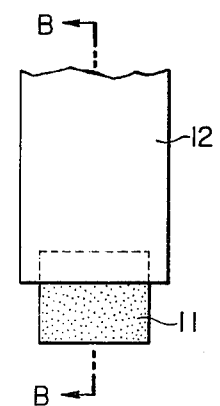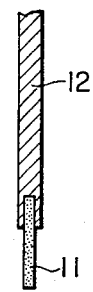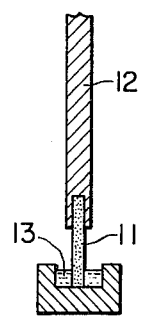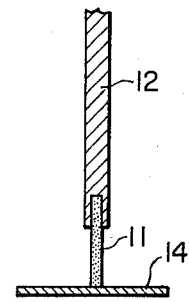
FIG. 6    FIG. 7
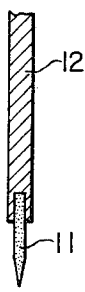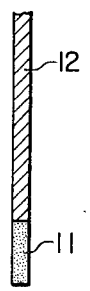

SAMPLE APPLICATOR

BACKGROUND OF THE INVENTION (a) Field of the Invention

The present invention relates to a sample applicator and, more particularly, to a sample applicator to be used in electrophoresis for applying a sample such as blood serum to a film.

(b) Description of the Prior Art

To analyze blood serum proteins etc. by electrophoresis, it is necessary to apply a sample such as blood serum taken from the patient onto a film such as a filter paper, cellulose acetate film or the like (hereinafter referred to as film). In electrophoresis, a fractionated pattern of sample is formed by energizing the film on which the sample is applied and that fractionated pattern is analyzed. To obtain a correct analyzing result, it is essential to apply the sample onto the film in a uniform straight line.

In the known method for applying the sample onto the film, the sample is sucked into a micropipette and a line of sample is drawn on the film by using a ruler. In such method, however, it is very inefficient and, moreover, it is difficult to apply the sample in a uniform and straight line. To eliminate the above-mentioned disadvantage, a method to use a blood serum applicator is known. As an example of blood serum applicators for that purpose, a blood serum applicator as shown in FIGS. 1A and 1B is known. That is, two thin plates 1 and 1' are arranged face to face by inserting a spacer 2 between them so that ends 1a and 1'a of thin plates 1 and 1' become parallel with each other. To apply a sample by using the above-mentioned blood serum applicator, the sample is absorb into the small gap 3 formed between the ends 1a and 1'a of thin plates 1 and 1' by means of capillarity and, then, applied onto the film. Another example of known blood serum applicators is constructed as shown in FIGS. 2A and 2B. That is, a V-shaped groove 4a is formed at an end of applicator body 4. This applicator is also arranged to absorb the sample into the V-shaped groove 4a by means of capillarity and, then, to apply the sample onto the film. These known applicators have the following disadvantages. That is, irregularity occurs in the absorbed sample because of surface tension of sample absorbed in the gap or groove at the end of applicator and, consequently, the sample applied onto the film becomes uneven. Moreover, if the applicator is held in the state that its end is inclined, the sample moves toward one side and, as a result, the applied sample becomes irregular. Besides, when the sample is applied by an inclined applicator, one-sided contact occurs between the applicator and film. As a result, the sample flows out onto the film from one end of gap or groove which contacts the film at first and, consequently, the applied sample becomes irregular.

SUMMARY OF THE INVENTION

It is, therefore, a primary object of the present invention to provide a sample applicator comprising an applicator blade made of porous material and provided at the end of holder, the sample applicator being arranged to absorb a sample by the applicator blade and, then, to apply the sample onto a film.

Another object of the present invention is to provide a sample applicator in which the applicator blade is demountably held by the holder.

Still another object of the present invention is to provide a sample applicator in which the applicator blade has a wedge-type sectional area.

BRIEF DESCRIPTION OF THE DRAWINGS

FIG. 1A shows a front view of a known sample application;

FIG. 1B shows a sectional view taken along the B—B line in FIG. 1A;

FIG. 2A shows a front view of another known sample applicator;

FIG. 2B shows a sectional view taken along the B—B line in FIG. 2A;

FIG. 3A shows a front view of a first embodiment of the sample applicator according to the present invention;

FIG. 3B shows a sectional view taken along the B—B line in FIG. 3A;

FIGS. 4 and 5 respectively show sectional views of the first embodiment at the time of sample application work;

FIG. 6 shows a sectional view of a second embodiment of the sample applicator according to the present invention; and FIG. 7 shows a sectional view of a third embodiment of the sample applicator according to the present invention.

DESCRIPTION OF THE PREFERRED EMBODIMENTS

In FIGS. 3A and 3B showing the first embodiment of the sample applicator according to the present invention, numeral 11 designates an applicator blade made of porous material such as foam plastic, foam rubber, ceramics, etc. and formed as a rectangular plate. Numeral 12 designates a holder which demountably holds the applicator blade 11 so that one end of applicator blade 11 projects from the holder 12.

The sample applicator according to the present invention is constructed as described in the above. To apply a sample to a film by using this sample applicator, the applicator blade 11 is at first dipped into the sample 13 as shown in FIG. 4. Thus, the sample 13 is absorbed into a large number of fine holes of applicator blade 11 by means of capillarity and, consequently, the applicator blade 11 is satisfactorily wetted by the sample. Then, the applicator blade 11 is pushed onto the film 14. Thus, it is possible to apply the sample onto the film 14. After applying the sample onto the film as described in the above, it is possible to use the applicator blade again for application of another sample by washing the applicator blade with water and drying it. Besides, it is also possible to replace the used applicator blade with a new one every time when applying a different sample.

The sample applicator according to the present invention described in the above has the following advantages. As the sample 13 is absorbed into a large number of fine holes of applicator blade 11, irregularity of absorption does not occur and, therefore, the applied sample does not become uneven. Even when the applicator blade 11 is inclined, the sample does not move toward one side. Moreover, when the applicator blade 11 is made of especially soft porous material, the applicator blade 11 is deformed and follows up the film 14 even when one-sided contact occurs between the applicator blade 11 and film 14 at the time of sample application. Due to the reasons described in the above, it is possible to apply the samples always uniformly when the sample applicator according to the present invention is used. Besides, as the applicator blade 11 is held by the holder 12 so that it can be freely mounted to and demounted from the holder 12 and it is possible to mount the applicator blade 11 to the holder 12 by only inserting the applicator blade 11, it is possible to replace the applicator blade 11 quite easily.

FIG. 6 shows a second embodiment of the sample applicator according to the present invention. In case of this embodiment, the end portion of applicator blade 11 is formed to that its section has a wedge-like shape. When this embodiment is used, it is possible to apply the sample in a fine straight line.

FIG. 7 shows a third embodiment of the sample applicator according to the present invention in which the applicator blade 11 is fixed to the holder 12 by a binding agent.

As described in the above, when the sample applicator according to the present invention is used, it is possible to apply the sample always uniformly. Moreover, as the applicator blade can be replaced easily, it is possible to apply different samples by replacing the applicator blade with a new one without washing the used applicator blade and this is very convenient.

I claim:

1. A new use for a blade of porous, liquid-absorptive material having a straight edge protruding at one end of a holder in which the blade of porous material is mounted, said new use comprising:

dipping the protruding blade edge into a liquid that is to be subjected to electrophoresis, in order to absorb a quantity of said liquid therein; and pushing the protruding blade edge against an electrically-energizable film sufficiently to express from the blade onto the film a fine, uniform, straight line sample of said liquid.

* * * * *